(12) United States Patent
Feygin et al.

(10) Patent No.: US 6,497,155 B1
(45) Date of Patent: Dec. 24, 2002

(54) ARTICLE COMPRISING A PARTICLE RETRIEVAL DEVICE

(75) Inventors: Ilya Feygin, Mountainside, NJ (US); Rhett L. Affleck, San Diego, CA (US); Aleksandr Grinberg, Old Bridge, NJ (US); Thuc H. Nguyen, Bensalem, PA (US)

(73) Assignee: Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 09/247,722

(22) Filed: Feb. 9, 1999

(51) Int. Cl.[7] .......................... G01N 35/10; G01N 35/02
(52) U.S. Cl. .................. 73/863.22; 73/864.11; 73/864.25; 422/63; 422/930; 436/54; 436/49
(58) Field of Search .............. 73/864.11, 864.22, 73/864.24, 864.25; 422/930, 63; 436/54, 49

(56) References Cited

U.S. PATENT DOCUMENTS

| | | | | |
|---|---|---|---|---|
| 3,932,141 A | * | 1/1976 | Beall et al. .................. 422/102 |
| 4,768,919 A | * | 9/1988 | Borgman et al. .............. 53/495 |
| 4,770,454 A | * | 9/1988 | Muscher et al. ........... 294/64.1 |
| 4,887,351 A | * | 12/1989 | Porterfield et al. ........... 29/740 |
| 4,937,048 A | * | 6/1990 | Sakai et al. .................... 422/63 |
| 5,280,979 A | * | 1/1994 | Poli et al. .................. 294/64.1 |
| 5,382,512 A | * | 1/1995 | Smethers et al. .............. 435/6 |
| 5,414,955 A | * | 5/1995 | Morin ...................... 47/1.01 R |
| 5,525,515 A | * | 6/1996 | Blattner ........................ 436/49 |
| 5,616,299 A | | 4/1997 | Walker et al. ................ 422/99 |
| 5,935,859 A | * | 8/1999 | Elliott et al. .................. 436/54 |
| 5,979,251 A | | 11/1999 | James et al. ............. 73/863.02 |
| 6,074,609 A | | 6/2000 | Gavin ......................... 422/99 |

FOREIGN PATENT DOCUMENTS

WO  WO99/49428  9/1999

OTHER PUBLICATIONS

"Update: New Combinatorial Chemistry," *Drug Discovery Today*, vol. 2, No. 6, pp. 214–216 (Jun. 1997).

* cited by examiner

*Primary Examiner*—Hezron Williams
*Assistant Examiner*—Michael Cygan
(74) *Attorney, Agent, or Firm*—DeMont & Breyer, LLC

(57) ABSTRACT

In one embodiment, a particle-retrieval device in accordance with the present teachings includes a receiver tube, vacuum-flow providing means and particle-disengaging means. The receiver tube is in fluid communication with the vacuum-flow providing means such that when flow is introduced into the vacuum-flow providing means, a suction or vacuum flow is developed at an end of the receiver tube. The suction causes a particle to adhere to the end of the receiver. A particle is disengaged by discontinuing the suction and, advantageously, by wetting the engaged particle.

21 Claims, 4 Drawing Sheets

ARTICLE COMPRISING A PARTICLE RETRIEVAL DEVICE

FIELD OF THE INVENTION

The present invention relates generally to an apparatus and method for retrieving a single small particle from a plurality of particles.

BACKGROUND OF THE INVENTION

Through combinatorial chemistry scientists can create combinatorial libraries of compounds, en masse, and rapidly test such libraries for physiological or other activity. The combinatorial libraries are generated by successively partitioning a group of solid supports, which are typically embodied as beads having a diameter in the range of about 50 to 1000 microns. With each successive partitioning, the solid supports are uniquely treated, such as by adding a chemical moiety thereto. The partitionings are repeated until a desired combinatorial library is produced. The combinatorial library comprises a large number of library compounds, each of which compounds is attached to a solid support.

For screening purposes, a combinatorial library is typically segregated into a plurality of small groups containing about 1–30 solid supports (i.e., library compounds) per group. The small groups of solid supports are usually retained in collection plates, referred to as microtiter or microwell plates, that have a multiplicity of small wells (e.g., 96-, 384-, 1536-well plates). To segregate a combinatorial library into such small groups, a device for handling a few or even an individual solid support is required. Such a device must be able to reliably withdraw a solid support from a large number of such solid supports contained in a fluid, and then deliver and deposit the withdrawn support to a desired site.

Aside from the difficulties inherent in handling an individual small particle, in the realm of combinatorial chemistry, a further complication arises. In particular, treatments steps (e.g., reaction steps, washing steps, etc.) often increase the tendency of the solid supports to adhere to one another or the transport/delivery means. Such increased adhesion complicates and frustrates individual particle retrieval.

Various devices are available for sorting, counting and retrieving particles from large groups of such particles. Such devices have been used for sorting or counting biological cells (U.S. Pat. Nos. 3,710,933; 4,173, 415; 4,606,631), transferring yeast containing beads (U.S. Pat. No. 4,655, 265), dispensing reagent spheres (U.S. Pat. No. 5,616,299), arraying small objects into containers (U.S. Pat. No. 5,649, 576), transferring articles contained in a fluid medium (U.S. Pat. No. 5,722,470) and placing a biological reagent on a substrate (U.S. Pat. No. 5,731,152). None of the above-referenced devices reliably retrieves a single particle from a group of such particles, transfers the retrieved particle to a desired destination, and deposits the particle at the desired destination.

More recently, a robot equipped with capillary tubes that pick up beads (i. e., solid supports) using a suction force has been disclosed. While such a device may reliably engage a particle, it will not reliably disengage the particle. More particularly, once a bead is engaged to a capillary tube, various physical phenomena cause an attraction between the bead and the capillary tube that tend to keep the bead engaged to the tube. Simply discontinuing suction will not reliably disengage the bead.

As such, an article and method for reliably retrieving, transferring and depositing a single particle is needed.

SUMMARY OF THE INVENTION

Satisfying the aforementioned need, a particle-retrieval device in accordance with the present teachings comprises, in some embodiments, a receiver tube, vacuum-flow providing means and particle-disengaging means. The receiver tube contains a bore or lumen running its full length. The bore is in fluid communication with the vacuum-flow providing means. When flow is introduced into the vacuum-flow providing means, a suction or vacuum flow is developed at the second end of the receiver. For the purposes of this Specification, when a first and a second region are described to be in "fluid communication," it means that fluid flow and/or pressure conditions prevailing in the first region affect fluid flow and/or pressure conditions in the second region.

The suction developed at the second end of the receiver causes a particle to adhere thereto. A particle-engagement site at the second end of the receiver is advantageously physically adapted to receive a single particle.

Once a particle is engaged to the receiver, various physical phenomena work in concert with the continuing suction force to keep the particle engaged. Such physical phenomena cause an increased adhesion between a particle and the receiver. As such, action in addition to discontinuing the suction force is required to reliably disengage a particle from the receiver tube. To that end, a particle-retrieval device in accordance with the present teachings advantageously incorporates particle-disengaging means.

In the illustrated embodiments, the particle-disengaging means advantageously delivers a droplet of liquid that is conducted to and wets an engaged particle. Discontinuing suction and wetting the particle reliably disengages the particle from the receiver.

To retrieve a particle from a source vessel requires that positioning means place the device and vessel in alignment and in sufficiently close proximity such that the suction developed at the particle-engagement site can "grab" a particle. In various embodiments, positioning means are configured to move either the particle-retrieval device, a source vessel or both. In one embodiment, the positioning means is an x-y-z stage.

In addition to the one particle that is engaged at the particle-engagement site, other particles and particle fragments may disadvantageously adhere to the receiver and/or the particle near the particle-engagement site. As such, in some embodiments, the present invention includes an excess particle/fragment remover for removing excess particles and particle fragments. The excess particle/fragment remover can be embodied in a variety of ways that are described later in this specification.

Since the present invention is capable of retrieving very small particles that may be difficult to directly observe, the present invention advantageously includes a particle detector. In one embodiment, the particle detector is realized as a bellows that is in fluid communication with the bore running through the receiver tube. As a particle engages the particle-engagement site at the second end of the receiver tube, pressure within the bore changes. Such a pressure change is observed as a collapse of the bellows (i.e., the bellows "compresses" or decreases in length). The change in bellows length can be detected and indicates that a particle is engaged.

Further features of the present invention will become apparent from the Detailed Description of specific embodiments thereof when read in conjunction with the accompanying drawings, which are described briefly below.

DETAILED DESCRIPTION OF THE INVENTION

The present invention finds particular utility for the retrieval and transfer of small spherical particles such as are typically used as solid supports for combinatorial chemistry. Such particles have a diameter that is typically in the range of about 50 to 1000 microns. The present invention can be tailored, in different embodiments, to retrieve particles having a diameter at the extremes of, or even beyond, the aforementioned range, or anywhere in between. A given particle-retrieval device is, however, advantageously limited to use over a somewhat smaller range of particle size. Such a smaller range should not limit the utility of the present invention since it is unlikely that the nominal diameter for a given type of solid support will vary by more than a factor of two or three.

Illustrative solid supports used for combinatorial chemistry and applicable for use in conjunction with the present invention include, without limitation, cellulose beads, controlled pore-glass beads, silica gels, polystyrene beads optionally cross linked with divinylbenzene and optionally grafted with polyethylene glycol and optionally functionalized with amino, hydroxy, carboxy, or halo groups, grafted copoly beads, polyacrylamide beads, latex beads, dimethylacrylamide beads optionally cross linked with N,N'-bisacryloyl ethylene diamine, glass and grafted plastic particles coated with hydrophobic polymer, and the like. Before such particles are handled using the devices and methods of the present invention, they have typically undergone a process of combinatorial synthesis, such as is described in U.S. Pat. No. 5,721,099.

It should be understood that reference to solid supports used in combinatorial chemistry is merely illustrative. The devices and methods described herein are useful for retrieving, transferring or depositing other types of small particles in other applications. In particular, such small particles are useful in molecular biology applications wherein DNA, RNA or the like is attached to the beads, and in immunology applications wherein antibodies are attached to the beads. For such applications, the beads typically have a diameter in the range of 1 to 15 microns. The present invention can be used for such applications. Moreover, the illustrated embodiments of the present invention may suitably be used for handling particles as large as several millimeters. Furthermore, while the present invention is advantageously used in conjunction with spherical particles, it is also useful for the retrieval of non-spherical particles having a smooth and regular surface topography.

Figure 1:
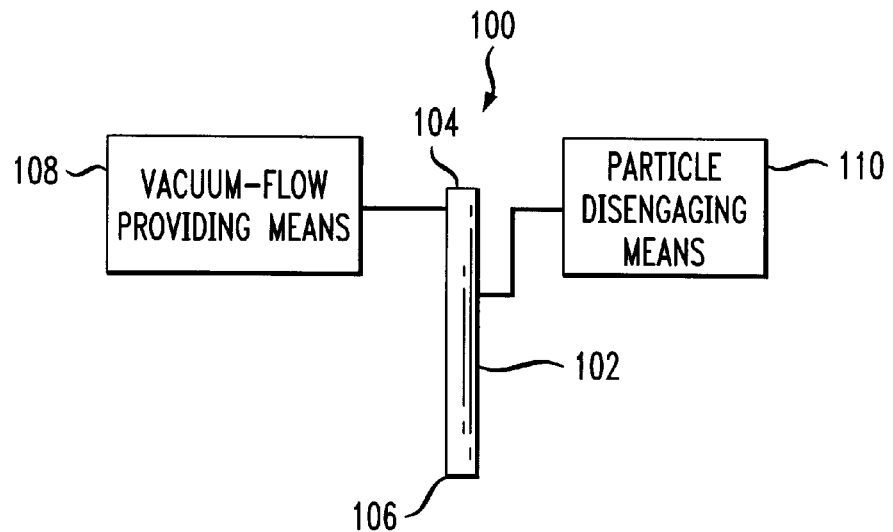
FIG. 1 is a simplified conceptual depiction of a device for retrieving a single particle in accordance with an illustrative embodiment of the present invention.

As depicted conceptually in FIG. 1, a particle-retrieval device 100 in accordance with the present teachings comprises a receiver 102, vacuum-flow providing means 108 and particle-disengaging means 110. First end 104 of receiver 102 is operatively connected to vacuum-flow providing means 108 such that the receiver is in fluid communication with the vacuum-flow providing means. Vacuum-providing means 108 is operable to develop a vacuum flow or suction at second end 106 of receiver 102. That suction provides a force that causes a particle to adhere to the second end of receiver 102, also referred to as the particle-engagement site. In some embodiments, the particle engagement site is physically adapted to receive a single particle, as described later in this Specification.

To disengage a particle from the particle-engagement site, the suction is discontinued. Various physical phenomena, predominantly molecular attractive forces, cause an adhesion between a particle and the receiver. Such molecular attractive forces include, among any others, van der Waals forces, hydrogen bonding, electrostatic forces and hydrophilic/hydrophobic effects. Such forces are hereinafter collectively referred to as "adhesion" or "adhesive forces." Due to such adhesion between a particle and the surface of receiver 102, discontinuing the suction, without more, will not reliably disengage a particle. As such, particle-disengaging means 110 is advantageously used for such purpose.

In the illustrated embodiments, particle-disengaging means 110 advantageously delivers a droplet of liquid that is conducted to, and wets (i.e., encapsulates) an engaged particle. The presence of the droplet brings several factors into play that collectively overcome the adhesive forces holding a particle to the receiver. In particular, the presence of the liquid generally reduces molecular interactions as a result of the change in dielectric constant (air versus the liquid). Moreover, the surface tension of the droplet tends to retain the particle therein. Discontinuing suction and encapsulating the particle in a droplet of liquid results in the reliable disengagement of a particle from the receiver.

Particle-disengaging means 110 can be realized in a variety of ways, a few of which are depicted in the Drawings and described later in this Specification.

Having provided a conceptual description of the present particle-retrieval device, the remainder of this Specification and the Drawings provide specific embodiments of such a device and its constituent elements.

Figure 2:
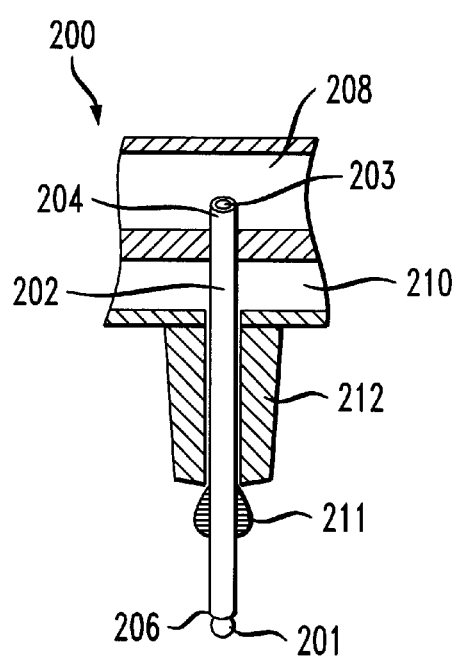
FIG. 2 depicts a particle-retrieval device in accordance with the embodiment of FIG. 1.

FIG. 2 depicts a first illustrative embodiment of a particle-retrieval device 200 in accordance with the present invention. In the illustrative embodiment depicted in FIG. 2, particle-retrieval device 200 includes a tube 202, a vacuum-providing manifold 208, and a liquid-delivery system, which, for illustrative device 200, comprises a liquid manifold 210 and a tube shroud 212, interrelated as shown. As to the correspondence between the structural elements of device 200 and those of conceptual particle-retrieval device 100: receiver 102 is realized as tube 202, vacuum-providing means 108 is realized as a vacuum-providing manifold 208 (and a fluid flow therethrough), and particle-disengaging means 110 is embodied as the liquid-delivery system.

Tube 202 has a bore or lumen 203 with termini at first end 204 and second end 206 of tube 202. First end 204 of tube 202 is disposed in vacuum-providing manifold 208 such that bore 203 is in fluid communication with the manifold.

To retrieve a particle from a vessel containing a group of such particles (hereinafter "source vessel") and typically, some liquid, a fluid flow (e.g., a vapor flow) is induced, introduced or otherwise provided in manifold 208 at a rate sufficient to induce a flow into bore 203 at second end 206 of tube 202. In other words, a suction force is developed at the particle-engagement site wherein bore 203 functions as a vacuum channel. Thus, a particle 201, typically in a liquid, is drawn to second end 206 of tube 202 by the induced flow (i.e., the suction) at second end 206 and adhered thereto due the pressure differential created across the particle as it obstructs the induced flow. As described later in this Specification, the particle-engagement site is advantageously adapted for engaging a single particle.

Since particles may have settled in the wells, etc., in which they are retained, the particles are advantageously stirred or agitated to facilitate the retrieval operation. Such stirring can be accomplished via a magnetic stirrer, or tube 202 itself can be used for such purpose.

The suction force developed at second end 206 of tube 202 must be maintained within an "acceptable" range. An acceptable suction force is defined herein as a force insufficient to substantially deform an engaged particle, but sufficient to reliably engage and hold a particle. It has been found that applying a partial vacuum within the range of about 22 to 27 mm Hg. develops a suction force at the particle-engagement site that satisfies the aforementioned criteria. In one embodiment, a suction-producing vapor flow developed in manifold 208 is generated via a vacuum pump, such as a 2-head, 2-stage TEFLON™ diaphragm pump (model MV2C) available from Vacuubrand of Fairfield, N.J. Selection of such a pump is within the capabilities of those skilled in the art.

Sufficient control must be maintained over the flow and pressure within manifold 208 and throughout particle-retrieval device 200 to ensure that a particle, once engaged, can be reliably and controllably disengaged (i.e., can be disengaged at will, yet will not prematurely disengage) from the device. Flow and/or pressure control valves advantageously provide such control. For example, a vacuum regulator with gauge, model no. 00910-10, commercially available from Cole-Palmer of Vernon Hills, Ill., is suitable for such purpose. The integration of such valves into the present system to provide flow and/or pressure control is within the capabilities of those skilled in the art.

The exterior of tube 202, but not bore 203, is in fluid contact with liquid manifold 210. Tube 202 passes through tube shroud 212. Liquid manifold 210 delivers, on demand, an amount of liquid. Shroud 212 protects tube 202 and ensures that at least some of the delivered liquid engages the exterior of tube 202. The solid-liquid interaction between the exterior of tube 202 and the liquid is advantageously controlled such that the liquid flows downwardly along the exterior of tube 202 in the form of a droplet 211 (hereinafter "particle-disengaging droplet"). Under gravitational forces, the particle-disengaging droplet flows towards the particle-engagement site.

At the particle-engagement site, the particle-disengaging droplet wets (e.g., encapsulates in liquid) engaged particle 201. As previously described, the liquid-encapsulated particle overcomes adhesive forces between the engaged particle and tube 202, such that the droplet and particle can disengage from the tube. To disengage a particle, the suction is discontinued and then the disengaging droplet is formed and conducted to the particle.

In some embodiments, a "blast" of air, etc., at greater than atmospheric pressure is directed through tube 202 in preparation for wetting an engaged particle. While such a blast typically will not reliably disengage a particle from tube 202, it will "flip" a particle from the particle-engagement site to the exterior surface of tube 202, where it is wetted by the particle-disengaging droplet.

Regarding droplet formation, a "critical surface tension" is associated with the wettability or release qualities of a material (i.e., the tube surface). Liquids with a surface tension below the critical surface tension of substrate will wet the surface, such that a droplet does not form. The critical surface tension is unique for any solid surface, and is determined by plotting the cosine of the contact angles of liquids of different surface tensions and extrapolating to cos $\theta=1$. At cos $\theta=1$, the contact angle of liquid is zero, such that the liquid wets the surface (i.e., the surface tension of the liquid is below the critical surface tension).

Thus, tube material and liquid is suitably selected to promote droplet formation. Moreover, various surface treatments can be applied to the tube to alter its wetting characteristics, as required. Organosilanes, such as, for example, methyltrichlorosilane, dimethyldichlorosilane, trimethylchlorosilane, their alkoxy derivatives, and hexamethyldisilazane are used to render substrates water repellent (i.e., water will not wet such a substrate, but rather form a droplet thereon). For example, glass can be dipped into a 5% to 10% solution of dimethyldiethoxysilane and heated for ten minutes at 120° C. to render the glass surface hydrophobic. Illustrative liquids for forming the particle-disengaging droplet include, without limitation, water, aqueous mixtures, aqueous alcohol solutions and acidic aqueous alcohol.

The amount of liquid ultimately delivered to engaged particle 201 should be controlled to ensure that such liquid does not overwhelm the liquid-holding capacity of a "receiver" vessel (i.e., the intended delivery site). To that end, the particle-disengaging droplet advantageously comprises an amount of liquid in the range of about 10 to about 50 microliters. Such an amount of liquid should not overwhelm a typical receiver vessel (e.g., the wells of a 96-well microtiter plate).

As previously stated, the particle-engagement site (i.e., second end 206 of tube 202) is advantageously physically adapted for engaging a single particle. In some embodiments, the adaptation is a "tip" (not shown in FIG. 2) that is disposed at second end 206 of the tube. The tip has various structural features that facilitate single-particle engagement. Moreover, in some embodiments, the tip is further configured to facilitate disengagement of the single particle. Furthermore, the tip is advantageously configured to prevent disengagement of a desired particle while disengaging other excess particles and particle fragments.

In addition to structural adaptations related to particle engagement and disengagement, the configuration of a tip may also depend on its material of construction. Suitable materials of construction include, without limitation, ceramic that has been silanized to promote hydrophobicity, glass, plastic, metal, sapphire inserts, bushing-type inserts in metal, and the like. The selected material must of course be compatible with the prevailing chemical/environmental conditions.

Several illustrative tips possessing structural adaptations for particle engagement and disengagement and which are suitable for use in conjunction with the present invention are described below and illustrated in FIGS. 3a–3c.

Figure 3A:
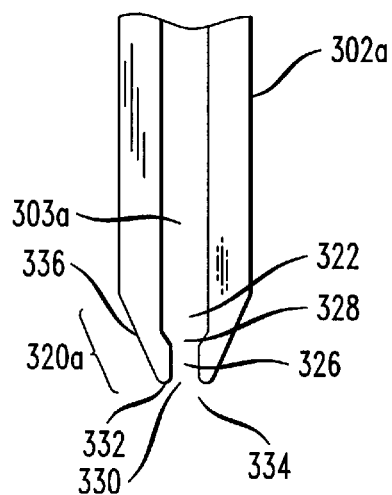
FIG. 3a depicts a first embodiment of a tip for engaging a particle.

FIG. 3a depicts a portion of tube 302a having bore 303a and a tip 320a that comprises glass or ceramic. Tip 320a has an outer diameter that is advantageously in the range of about 1.25 to 1.75 millimeters. Tip 320a has an internal channel or bore 322 that is in fluid communication with bore 303a and thus functionally becomes a part of the vacuum channel. Bore 322 has a diameter that is advantageously chosen to provide the maximum flow through tip 320a (i.e., maximize suction) based on the fluid flow in the vacuum-providing manifold 208. Typically, the diameter of bore 322 is equal to the diameter of bore 203. Tip 320a has an outer diameter that is advantageously in the range of about 1.25 to 1.75 millimeters (mm).

It will be appreciated that bore 322 may have a diameter larger than the subject particles. As such, the tip must not allow an engaged particle to be drawn completely into the vacuum channel (i.e., bore 322/203). In one embodiment, a fine screen or mesh (not shown) is disposed over the end of the tip. Such a screen will, however, result in some loss in suction force. In the present embodiment, tip 320a advantageously includes a reduced-diameter bore 326 sized to engage particles of a selected diameter such that the particles cannot enter the bore. First end 328 of reduced-diameter bore 326 is in fluid communication with bore 322. Second end 330 of bore 326 is coincident with apex 334 of tip 320a, which is the site at which a particle engages the tip.

Second end 330 of bore 326 is adapted to improve particle-holding capability. For spherical-shaped particles, such as the solid supports used for combinatorial-chemistry libraries, second end 330 of bore 326 is advantageously chamfered or beveled. Such chamfering or beveling provides additional surface for supporting the solid support. When tip 320a comprises glass, second end 330 of bore 326 is chamfered by a melting process (typically called "flaming") or by machining. Ceramic tips are chamfered by machining, forming or molding processes.

In some embodiments, second end 330 terminates at region 332 having a slight enlargement in diameter. Such an enlarged-diameter region (relative to reduced-diameter bore 326) exposes more of the surface area of a particle to the suction force, thereby enhancing or strengthening the engagement of the particle to the tip.

Ceramic and glass tips advantageously include a structural adaptation for guiding the particle-disengaging droplet towards the engaged particle. Such a structural adaptation is considered to be an element of the particle-disengagement means. In illustrative tip 320a, the structural adaptation comprises tapered exterior portion 336. In embodiments in which a blast of higher pressure air, etc., is provided in preparation to wetting an engaged particle, the particle is typically "flipped" from apex 334 to the tapered exterior portion 336 of tip 320a.

Figure 3B:
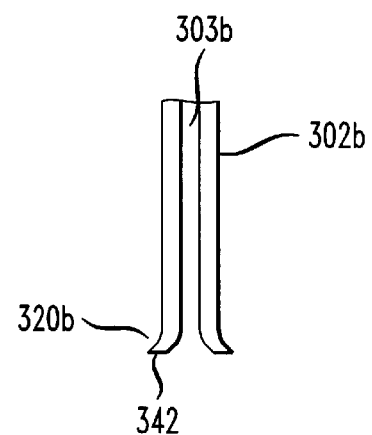
FIG. 3b depicts a second embodiment of a tip for engaging a particle.

FIG. 3b depicts a portion of a tube 302b having bore 303b and tip 320b. Tip 320b comprises metal, and has an outside diameter that is advantageously in the range of 0.5 to 1.75 mm. Tip 320b includes flared end 342 for engaging a spherical particle. Tip 320b is advantageously used for particles having a diameter of 0.5 mm or larger. In some embodiments, tube 302 is realized as a hypodermic needle.

Figure 3C:
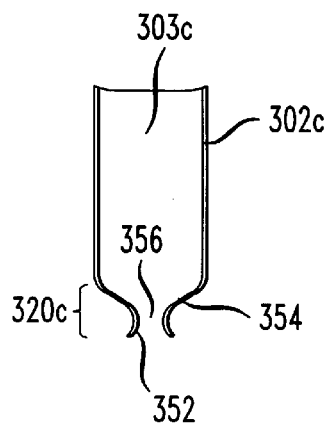
FIG. 3c depicts a third embodiment of a tip for engaging a particle.

FIG. 3c depicts a portion of a tube 302c having bore 303c and tip 320c. Tube 302c and tip 320c comprise a relatively thin layer of metal compared to tube 302b of FIG. 3b. Tip 320c is advantageously used for particles having a diameter of 0.1 mm or larger. For engaging spherical particles, tip 302c advantageously includes flared end 352. The outside diameter of tip 320c is advantageously in the range of 0.5 to 1.75 mm. Tip 320c includes tapered portion 354 which tapers to a minimum diameter at region 356. Tapered portion 354 prevents a particle from entering tip 320c.

In the illustrative particle-retrieval device 200 depicted in FIG. 2, the liquid-delivery system delivered a particle-disengaging droplet in a coaxial manner about tube 202 via the arrangement of liquid manifold 210 and shroud 212. In another embodiment, which is depicted in FIG. 4, the liquid-delivery system comprises a liquid manifold (not shown) and a liquid-delivery conduit 412 that receives liquid from the liquid manifold and delivers a particle-disengaging droplet 411 along a portion of the exterior of the tube.

Figure 4:
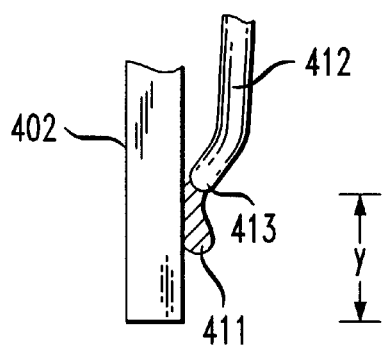
FIG. 4 depicts an alternate embodiment of a liquid-delivery system for use in conjunction with an illustrated embodiment of the present invention.

In the illustrative embodiment depicted in FIG. 4, liquid-delivery conduit 412 is disposed adjacent to and abutting tube 402 (tip detail not shown). Orifice 413 of tube 412 is disposed at a distance y from the particle-engagement site of tube 402, where distance y is advantageously in the range of about one hundred to several hundred percent of the outside diameter of larger-diameter tubes comprising glass, etc., and at least about 1 mm for smaller diameter tubes comprising metal, etc.

A tendency exists for fragments to adhere to the present device at or near the particle-engagement site. Such a tendency is due, in part, to the aforedescribed molecular attractive forces, and, in some cases, to an increase in adhesiveness due to exposure of the particles to various reaction steps, wash steps and the like. As such, in some embodiments, the present particle-retrieval device advantageously includes an excess particles/fragment remover.

Figure 5:
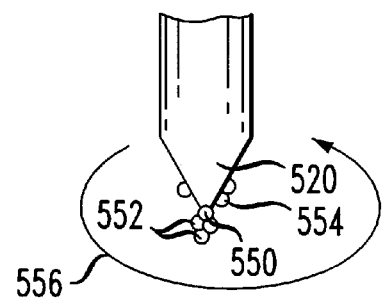
FIG. 5 depicts a conceptual depiction of a first embodiment of a fragment remover for use in conjunction with the present invention.

The excess particles/fragment remover imparts a force to adhered fragments that is capable of dislodging the fragments. In a first embodiment, which is conceptually depicted in FIG. 5, drag forces are developed by moving tip 520 through liquid, such as the liquid retained in the source vessel. At some velocity, the drag force acting on the excess particles 552 and fragments 554 overcomes the various adhesive forces that hold such particles and fragments to the one desired engaged particle 550 (or to surface of the receiver). At that velocity, the excess particles and fragments dislodge. Since particle 550 engaged at the particle-engagement site is held thereto by the suction force, in addition to molecular adhesive forces, that particle does not disengage when the excess particles and fragments are removed.

An excess particles/fragments remover can be realized by a means that allows the source vessel and the tube/tip of the particle-retrieval device to be moved relative to one another. Since the particles may be retained in micro-wells or other small volumes, such relative movement much be appropriate for small areas. Reciprocative- or orbital-type motion is well suited for such an application. In the embodiment depicted in FIG. 5, tip 520 moves in orbital motion, as indicated via vector 556.

In one illustrative embodiment, the source vessel is disposed on a device capable of imparting such orbital motion.

The motion of the source vessel, and the liquid it holds, generates the aforementioned drag force. One such device is described in the assignee's co-pending U.S. Pat. Application entitled "Agitation Device" filed Jul. 29, 1998 as Ser. No. 09/124,497. That device comprises a movable assembly that is suspended by resilient supports from a frame. The movable assembly includes spaced upper and lower plates having a rotatably-supported member disposed therebetween. The mass of the rotatably-supported member is asymmetrically distributed about its rotational axis. A drive means causes the rotatably-supported member to rotate. Due to the asymmetric mass distribution of the rotatably-supported member, force is non-uniformly applied to the resilient supports by which the movable assembly is suspended. The movable assembly, and the particle-retrieval device supported thereon, are thereby placed in orbital motion.

As an alternative to placing the source vessel in motion, the tube/tip of the particle-retrieval device can be placed in motion. Either the particle-retrieval device can be placed on the aforedescribed "Agitation Device," or the particle-retrieval device itself can be structured such that it is suspended in the manner of the above-described movable assembly and have a rotatably-supported member having an asymmetric mass distribution attached thereto.

In another embodiment, an excess particles/fragments remover is a device operable to apply an electrostatic charge having a polarity and amplitude suitable for disengaging the adhered fragments. The applied charge diffuses any electrostatic attraction between fragments and the tip which may be sufficient to disengage excess particles and fragments.

As previously described, the present device may be used for retrieving exceedingly small particles. As such, unaided visual reconnaissance may be insufficient for determining whether or not a particle has been retrieved. To that end, in some embodiments, the present invention further comprises a particle detector. Particle detection can be implemented in a variety of ways, a few of which are described below.

Since an engaged particle will obstruct flow through the vacuum channel (e.g., bore 203 in FIG. 2), a flow meter can be used, in one embodiment, as a particle detector. Those skilled in the art will be able to select a flow meter suitable for flow detection at the prevailing flow rates. In another embodiment based on flow detection, a conductivity detector is used to monitor the conductivity of liquid flowing through the end of the tip or bore. As flow substantially ceases upon particle engagement, a change in conductivity will be observed. In a further embodiment, an optical detector can be used for detecting whether a particle is engaged to the present particle-retrieval device. Such optical detectors are familiar to those skilled in the art.

Figure 6A:
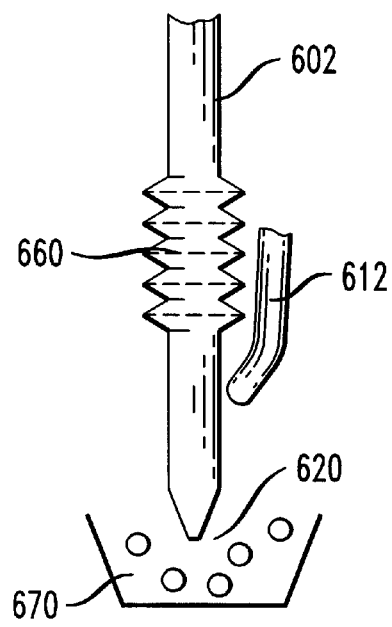
FIG. 6a depicts an illustrative embodiment of a particle detector comprising a bellows, wherein the bellows is in an un-collapsed state.
Figure 6B:
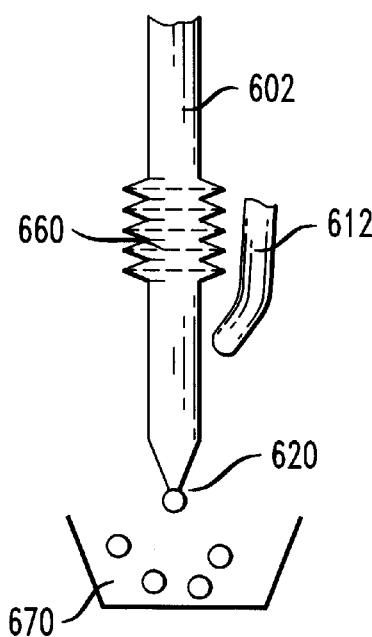
FIG. 6b depicts the bellows of FIG. 6a in a partially collapsed state.

An implication of the aforedescribed decrease in flow through the vacuum channel with particle engagement is that internal negative pressure increases. Thus, in another embodiment, a particle detector is a device operable to detect an increase in negative pressure in the vacuum channel. In one embodiment, such a device is realized as a bellows. FIGS. 6a and 6b depict an in-line bellows 660.

FIG. 6a depicts bellows 660 disposed in the vacuum channel, typically in-line with tube 602. In FIG. 6a, bellows 660 is depicted in an un-collapsed state before a particle is retrieved from source vessel 670 and engaged to tip 620. FIG. 6b depicts bellows 660 after collapse due to the increased negative pressure that results when a particle engages tip 620. Thus, by determining the condition (i.e., un-collapsed vs. collapsed) of bellows 660, it can be determined whether or not a particle is engaged to tip 620.

Moreover, bellows 660 advantageously functions as a fragment detector, as well. To the extent that an irregularly-shaped fragment engages tip 620, flow and pressure will not be affected to the same extent as when a particle is attached. When such a fragment engages tip 620, bellows 660 will not collapse to the same extent as when a particle is attached.

Bellows 660 can be monitored to determine its condition with the unaided eye, or by a variety of sensors, including, without limitation, optical sensors, electrical sensors, electromechanical sensors, and electromagnetic sensors familiar to those skilled in the art. Bellows suitable for use in conjunction with the present invention include, without limitation, nickel alloy bellows that are commercially available from Servometer Corporation of Cedar Grove, N.J. Bellows having an un-collapsed length in the range of about 10 to 30 mm, which reduce in length upon partial collapse by about 5 mm, have been found to be suitable for use in conjunction with the present invention.

Liquid-delivery conduit 612 advantageously delivers a particle-disengaging droplet (not shown) to the exterior of tube 602 between bellows 660 and tip 620 to ensure that bellows 660 will not affect the integrity of the droplet.

To retrieve a particle from a source vessel using the present device, and to deposit it in a "receiver vessel," a positioning means is advantageously used. Such a positioning means (1) accurately positions the particle-retrieval device relative to the source and/or receiver vessels, or (2) accurately positions the vessels relative to the device, or (3) positions both the device and the vessels.

Thus, in some embodiments of the present invention, the particle-retrieval device advantageously includes positioning means. In a first embodiment, the positioning means comprises at least one x-y-z stage that is operable to precisely position the source vessel and/or the receiver-vessel relative to the present particle-retrieval device, or vice versa. In a second embodiment, the particle-retrieval device, or a portion thereof, is movable in the z-direction, while at least one x-y stage is used for positioning the source and receiver vessels in the x- and y-directions. Combinations of and variations on the aforedescribed specific embodiments provide those skilled in the art with a large number of possible positioning arrangements for use in conjunction with the present invention.

Figure 7:
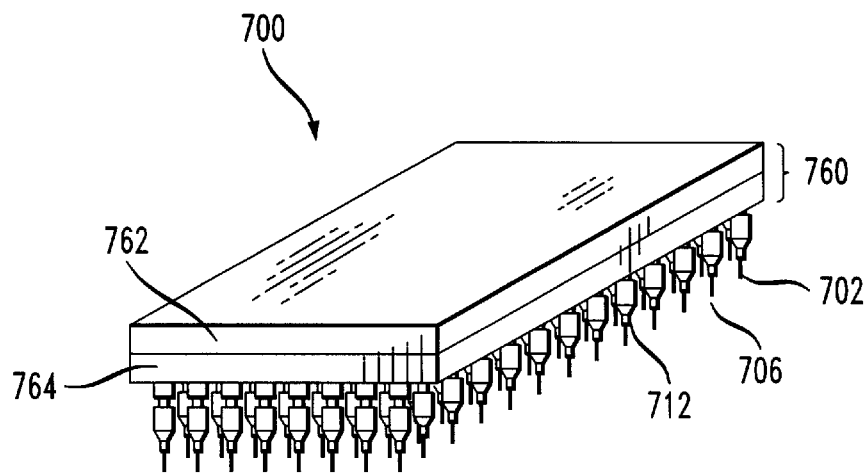
FIG. 7 depicts a particle-retrieval device adapted for single-particle retrieval at a plurality of sites.

In view of the large size of a typical combinatorial-chemistry library, sampling requirements may require performing multiple particle-retrieval operations. Carrying out such multiple operations seriatim with a particle-retrieval device capable of retrieving only a single particle per operation is likely to be impractical due to time constraints. Particle-retrieval device 700, depicted in FIG. 7, addresses such a limitation.

Particle-retrieval device 700 has the functionality of a plurality of the previously-described devices (e.g., device 200). In particular, device 700 comprises a plurality of tubes 702 depending from platform 760. Each tube 702 has a bore (not shown). A tip (not shown), embodiments of which have been previously described, advantageously depends from a second end 706 of tube 702. Thus, tube 702 is configured in the manner of tube 202.

Device 700 also includes a liquid-delivery system such as those previously described. For clarity of illustration, the liquid-delivery system depicted for device 700 includes a tube shroud 712 and is configured in the manner of the liquid-delivery system of device 200 of FIG. 2. In another embodiment, the liquid-delivery system includes a liquid-delivery conduit that is disposed adjacent to and abutting tube 702 near the particle-engagement site in the manner of the liquid-delivery system depicted in FIG. 4.

A first end (not shown) of each tube 702, and more particularly the bore of each tube, is in fluid communication with a vacuum-providing manifold (not shown). The exterior of tube 702 is in fluid contact with a liquid manifold (not shown). As previously described, the liquid manifold delivers an amount of liquid that engages the exterior of tube 702 and flows downwardly thereon in the form of a particle-disengaging droplet that wets an engaged particle.

Since a given multi-well source or receiver vessel will typically be characterized by a unique geometry and size (e.g., 96-well vs. 384-well vs. 1536-well microtiter plates), particle-retrieval device 700 is advantageously physically adapted for vessel-specific particle retrieval and delivery. More particularly, inter-tube spacing and geometry are pre-selected so that when device 700 and the source/receiver vessels are aligned, each tube 702 aligns with a desired region (e.g., well, etc.) of that vessel. For example, given a standard 96-well microtiter plate, which comprises an 8×12 array of wells with a center-to-center well spacing of 9 mm., tubes 702 are arranged, in one embodiment, in a complementary 8×12 array with a center-to-center spacing of 9 mm within platform 760.

In illustrative particle-retrieval device 700, platform 760 comprises detachably-coupled upper section 762 and lower section 764. Tubes 702 depend from lower section 764. Upper section 762 includes the vacuum-providing manifold (not shown) and the liquid manifold (not shown). The manifolds of upper section 762 are advantageously designed to be insensitive to the layout of tubes 702. That is, such manifolds are integrable with any of a variety of specific layouts of tubes 702 within lower section 764. In this manner, a variety of vessel-specific lower sections 764 can be interchangeably coupled to standard upper section 762.

The aforedescribed integration of vessel-specific lower section 764 and standard upper section 762 can be accomplished using any one of a variety of well known interfacing means/techniques such as by incorporating vessel-specific auxiliary headers within lower section 764. A first vessel-specific auxiliary header includes a vessel-specific group of orifices that receive a first end of each tube 702, and a second standard orifice (or standard group of orifices) for engaging the vacuum-providing manifold of upper section 762 in direct fluid communication. In such a manner, the bore of each tube 702 is placed in fluid communication with the vacuum-providing manifold. A second vessel-specific auxiliary header interfaces with the liquid manifold of upper section 762 for delivering a particle-disengaging droplet to the exterior of each tube 702.

In an alternate embodiment, platform 760 is vessel specific and comprises a single section in which the bore of each tube is in direct fluid-communication with the vacuum-providing manifold and the exterior of each tube 702 receives a particle-disengaging droplet via a liquid-delivery system.

A previous example considered a 96-well microtiter plate comprising an 8×12 array of wells as a source/receiver vessel. In that example, an illustrative particle-retrieval device suitable for servicing the plate (i.e., retrieving/delivering particles) comprised an 8×12 array of tubes. In other embodiments, a particle-retrieval device suitable for servicing such a vessel has a lesser number of tubes arranged in such a manner that with successive retrieval/delivery operations, all 96 wells can be serviced. For example, in one embodiment, a suitable device comprises eight tubes each having a particle-engagement site. The tubes are appropriately spaced for alignment with a column of 8 wells in the 96-well plate. Thus, with 12 repetitive operations, all 96 wells can be serviced.

While servicing a 96-well microtiter plate will usually take longer with an eight-tube device than with a ninety six-tube device, the service time for the eight-tube device is not impractically long. For example, an eight-tube device has serviced a 96-well microtiter plate in about one minute. The total time required for each one of twelve repetitive sequences was about 5 seconds. The repetitive sequence breaks down as follows: 0.5 seconds for particle retrieval, 1 second to remove undesired fragments, 2 seconds to transfer the engaged particle to a second site for particle delivery, and 1.5 seconds to disengage/deliver the liquid-encapsulated particle.

Figure 8:
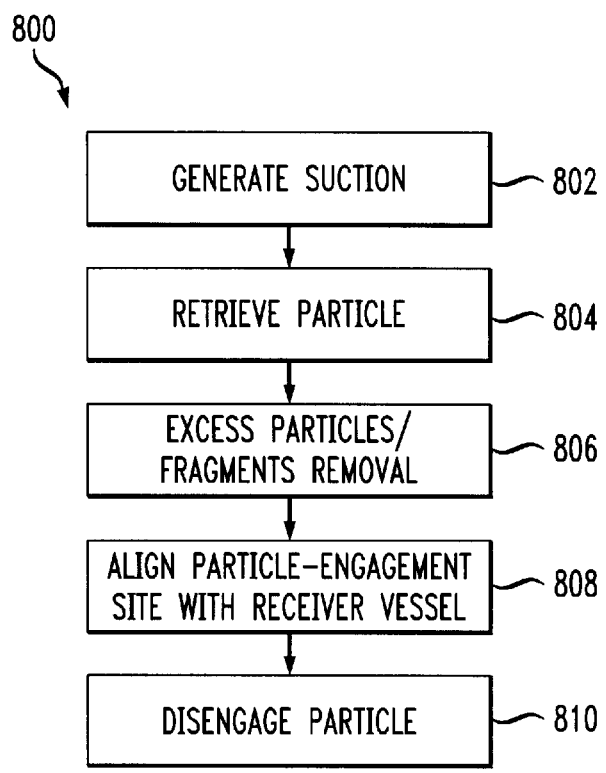
FIG. 8 depicts, via flow diagram, a method in accordance with an illustrative embodiment of the present invention.

The present invention also provides a particle retrieval/delivery method 800. FIG. 8 depicts, via flow diagram, an illustrative embodiment of method 800.

In accordance with operation 802 of method 800, suction is generated at a particle-engagement site of a particle-retrieval device. This is accomplished, in one embodiment, in the manner previously described. After establishing suction, a particle is retrieved as per operation 804. In some embodiments, particle retrieval comprises a positioning step wherein the particle-retrieval device and a source vessel are aligned and moved into the immediate vicinity of one another such that the particle-engagement site can engage a particle. In the manner previously described, either the particle-retrieval device, the source vessel or both the device and the vessel can be moved during the positioning step. The particles are advantageously agitated to facilitate particle engagement.

After particle engagement, excess particles and particle fragments are advantageously disengaged from the vicinity of the particle-engagement site in operation 806. Excess particles/fragments removal can be effected in any of the aforedescribed ways. For particle delivery to a receiver vessel, method 800 also includes a second positioning step 808 wherein the particle-engagement site of the particle-retrieval device and a receiver vessel are brought into alignment.

After alignment, an engaged particle is disengaged into the receiver vessel in operation block 810. The disengagement operation advantageously comprises discontinuing the suction generated in operation 802, and then wetting the particle. In some embodiments, a blast of high pressure air or other gas is sent through the receiver before wetting to facilitate the wetting operation as previously described.

It is to be understood that the embodiments described in this specification are merely illustrative of the invention and that many variations may be devised by those skilled in the art without departing from the scope and spirit of the invention. It is therefore intended that such variations be included within the scope of the following claims and their equivalents.

We claim:

1. An apparatus comprising:
   a vacuum source for providing a vacuum;
   a tube having an exterior, and a bore, wherein said bore is in fluid communication with said vacuum source;
   a tip that is disposed at an end of said tube, wherein said tip is in fluid communication with said bore, and wherein said tip terminates in a particle-engagement site that is physically adapted to receive a single particle; and means physically adapted for removing said single particle with a droplet of liquid.

2. The apparatus of claim 1 and further comprising:

a positioner that moves at least one of either the tube, a source vessel or a receiver vessel along at least one of three spatial axes, including an x-axis, a y-axis and a z-axis.

3. The apparatus of claim 1 wherein said means comprises a liquid-delivery system that delivers a droplet of liquid to said exterior of said tube at least 1 millimeter from said particle-engagement site, and wherein said tip tapers to an apex at said particle-engagement site.

4. The apparatus of claim 1 wherein said exterior of said tube comprises a surface treatment to promote droplet formation.

5. The apparatus of claim 1 and further comprising an excess particles/fragment remover that dislodges undesired particles and particle fragments that adhere to a desired particle that engages said tip at said particle-engagement site or that adhere to said tube or tip near said particle-engagment site.

6. The apparatus of claim 1 and further comprising a particle detector that indicates the presence of a desired particle that engages said tip at said particle-engagement site.

7. The apparatus of claim 6 wherein said particle detector detects a change in flow through said bore.

8. The apparatus of claim 6 wherein said particle detector optically detects said desired particle.

9. The apparatus of claim 6 wherein said particle detector detects a change in pressure in said bore.

10. The apparatus of claim 9 wherein said particle detector comprises a bellows that is in fluid communication with said bore in said tube.

11. The apparatus of claim 10 wherein said particle detector further comprises a sensor for sensing a change in state of said bellows responsive to said change in pressure in said bore, wherein said sensor is selected from the group consisting of optical sensors, electrical sensors, electromechanical sensors, and electromagnetic sensors.

12. The apparatus of claim 1 wherein said vacuum source comprises a vacuum manifold.

13. The apparatus of claim 12 wherein said vacuum source further comprises a vacuum generator for producing a vapor flow in said vacuum manifold.

14. The apparatus of claim 1 wherein the liquid-delivery system comprises a liquid manifold for dispensing liquid.

15. An apparatus comprising:

a platform;

a vacuum manifold that is disposed within said platform;

a plurality of tubes that depend from said platform, each tube having a bore that is in fluid communication with the vacuum manifold;

a tip that is disposed at an end of each tube, wherein said tip is in fluid communication with said bore, and wherein said tip terminates in a particle-engagement site that is physically adapted to receive a single particle; and means physically adapted for removing said single particle with a droplet of liquid, said means comprising a liquid-delivery system that delivers said droplet of liquid to an exterior of each said tube at least 1 millimeter from said particle-engagement site, wherein said liquid delivery system comprises a liquid manifold that is disposed within said platform;

wherein said tip has a structural adaptation that guides said droplet to said particle-engagement site.

16. The apparatus of claim 15 wherein said platform comprises a first detachably-coupled portion and a second detachably-coupled portion, wherein said plurality of tubes depends from said first detachably-coupled portion, and said vacuum manifold and said liquid manifold are disposed with said second detachably-coupled portion.

17. A method comprising:

generating suction at a particle-engagement site;

retrieving a desired particle;

discontinuing suction; and after suction is discontinued, directing a droplet of liquid toward said desired particle.

18. The method of claim 17 further comprising removing undesired particles and particle fragments from a region near said particle-engagement site, wherein said removal occurs before said droplet of liquid is directed toward said desired particle.

19. The method of claim 18 further comprising detecting whether said desired particle is engaged at said particle-engagement site.

20. The method of claim 18 further comprising detecting whether a fragment is engaged at said particle-engagement site.

21. The method of claim 17 wherein the operation of directing a droplet of liquid toward said desired particle further comprises delivering a blast of positive pressure to said particle-engagement site.

\* \* \* \* \*